United States Patent [19]

Garleb et al.

[11] Patent Number: 5,308,832

[45] Date of Patent: May 3, 1994

[54] NUTRITIONAL PRODUCT FOR PERSONS HAVING A NEUROLOGICAL INJURY

[75] Inventors: Keith A. Garleb, Powell; Stephen J. DeMichele, Dublin; Linda S. Rausch, Blacklick; Martha K. Fuller, Columbus; Stephen R. Behr, Westerville, all of Ohio

[73] Assignee: Abbott Laboratories, Abbott Park, Ill.

[21] Appl. No.: 920,087

[22] Filed: Jul. 27, 1992

[51] Int. Cl.$^5$ .............................................. A61K 37/02
[52] U.S. Cl. ........................................ 514/2; 514/21; 426/656; 426/800
[58] Field of Search ....................... 514/2, 21; 426/656, 426/800

[56] References Cited

U.S. PATENT DOCUMENTS

| | | | |
|---|---|---|---|
| 4,263,286 | 4/1981 | Nakajima et al. | 424/199 |
| 4,874,603 | 10/1989 | Fratzer | 424/10 |
| 4,880,912 | 11/1989 | Callison | 530/361 |

OTHER PUBLICATIONS

"Moderate hyperglycemia augments ischemic brain damage: A neuropathologic study in the rat", Pulsinelli et al., *Neurology*, 32:1239–1246 (1982).

"The predictive value of cerebral anaerobic metabolism with cerebral infarction after head injury", Robertson et al., *Neurosurgery*, 67:361–368 (1987).

"Ischemic brain damage is still common in non-missile head injury", Graham et al., *Journal of Neurology, Neurosurgery and Psychiatry*, 52:346–350 (1989).

"A stroke model designed for preclinical study", Hsu et al., in *Cerebral Ischemia and Resuscitation*, Schurr et al. editors, CRC Press, pp. 47–57 (1990).

"Cerebral circulation and metabolism after severe traumatic head injury: the elusive role of ischemia", Bouma et al., *Journal of Neurosurgery*, 75:685–693 (1991).

"Hyperglycemia and neurological outcome in patients with head injury", Lam et al., *Journal of Neurosurgery*, 75:545–551 (1991).

"Dietary Nonprotein Calories and Cerebral Infarction Size in Rats", Robertson et al, *Stroke*, vol. 23, No. 4, pp. 564–568 (Apr. 1992).

Sales Literature for OSMOLITE® and OSMOLITE®HN, ©1993, Ross Laboratories.

"Carbohydrate metabolism in man: effect of elective operations and major injury", Long et al., *Journal of Applied Physiology*, vol. 3, No. 1, Jun. 1971, pp. 110–116.

"Effects of Serum Glucose Concentration on Brain Response to Circulatory Arrest", Meyers et al., *Journal of Neuropathology and Experimental Neurology*, 35:301 (1976).

"Clinical restitution following cerebral ischemia in hypo-, normo- and hyperglycemic rats", Siemkowicz et al., *ACTA Neurologica Scandinavica*, 58:1–8 (1978).

"Deleterious Effect of Glucose Pretreatment on Recovery from Diffuse Cerebral Ischemia in the Cat", Ginsberg et al., *Stroke*, vol. II No. 4 (1980) pp. 347–354.

"Brain Lactic Acidosis and Ischemic Cell Damage: 1. Biochemistry and Neurophysiology", Rehncrona et al., *Journal of Cerebral Blood Flow and Metabolism*, 1:297–311 (1981).

"Monoacetin and protein metabolism during parenteral nutrition in burned rats", Maiz et al., *Journal of Biochemistry*, 226:43–50 (1985).

"Ketone precursors as nutritional substrates may improve neurological outcome following ischemia", Peek et al., *Journal of Neurotrauma*, 6:205–206 (1989).

"Intensive Management of Severe Head Injury", Borel et al., *Chest*, Jul. 1990, pp. 180–189.

"Effect of plasma glucose on infarct size in focal cerebral ischemia-repurfusion", Yip et al., *Neurology*, 41:899–905 (1991).

*Primary Examiner*—Howard E. Schain
*Assistant Examiner*—Choon Koh
*Attorney, Agent, or Firm*—Lonnie R. Drayer; Donald O. Nickey

[57] ABSTRACT

An enteral nutritional product for a person having a neurological injury is very low in carbohydrate, but high in fat. The fat is supplied by a lipid blend having a ratio of n-6 to n-3 fatty acids in the range of 1 to 6. Preferably the nutritional product contains nutrients having antioxidant properties, for example beta-carotene, vitamin E, vitamin C, taurine, molybdenum and selenium.

19 Claims, 2 Drawing Sheets

FIG-1

FIG-2

NUTRITIONAL PRODUCT FOR PERSONS HAVING A NEUROLOGICAL INJURY

FIELD OF THE INVENTION

The present invention relates to a nutritional product for persons having a neurological injury, such as from trauma to the head.

BACKGROUND OF THE INVENTION

The phenomena of head injury is well described in "Intensive Management of Severe Head Injury", Borel et al, CHEST, July, 1990, pages 180-189, at page 181. Cerebral injuries may be of either the penetrating or non-penetrating varieties, both of which cause damage to the brain and vasculature structures. Secondary injury to the brain indicates a vicious circle of escalating injury. Cerebral injury causes cerebral edema, cerebral edema raises intracranial volume which increases intracranial pressure, raised intracranial pressure compresses brain tissue and decreases cerebral perfusion pressure further increasing cerebral injury. Decreases in cerebral perfusion pressure result in cerebral blood flow falling below the level necessary to prevent neurologic ischemia and cell injury. When compartmental pressure gradients are established by local areas of injury, transcompartmental herniation of brain tissue results in catastrophic neurologic injury.

Nutritional support of the patient with a neurological injury is a complex problem. Patients with a severe head injury are hypermetabolic and catabolic, and they require early and intensive nutritional support to minimize malnutrition-related complications. Nutritional support may, however, adversely affect neurological recovery. Experimental studies have shown that hyperglycemia due to glucose infusion or to the postprandial state worsens neurological recovery from cerebral and spinal cord ischemia. The mechanism of this detrimental effect is not completely understood, however, in many studies hyperglycemia has been associated with increased accumulation of lactic acid. Development of a diet which would supply protein and caloric needs without adversely affecting neurological recovery would have widespread use in patients with central nervous system ischemia or trauma.

Glucose tolerance of critically ill patients receiving nutritional support is an important concern of nutritional support personnel. Several studies have demonstrated that injured and critically ill patients have increased rates of glucose production and glucose oxidation which are not easily suppressed by exogenous glucose administration. It has been demonstrated that accelerated gluconeogenesis can not be reduced by administration of exogenous glucose at rates which would normally suppress glucose production. Very high levels of blood glucose can result with the administration of an exogenous source of carbohydrate because the patient is in a persistent gluconeogenic state and has a blunted insulin response, a decreased tissue sensitivity to insulin and/or an impaired peripheral utilization of glucose.

As with critically ill patients in general, hyperglycemia is frequently associated with severe head injury. In the course of alimenting patients with a severe head injury, the hyperglycemic response can be exaggerated by the feeding of conventional alimentation formulas which use glucose as the major nonprotein caloric source. Hyperglycemia has been associated with poor neurological outcome. The late neurological sequelae of cerebral ischemia are consistently worse when the blood glucose level is elevated during ischemia, suggesting that lactic acidosis or other metabolic consequences of glucose metabolism damages nervous tissue.

Fasting has been used as a means to reduce blood glucose following head injury. However, it has been reported that malnutrition can lead to suppression of immune responses and poor wound healing. Also, failure to treat the hypermetabolic response in head injury is probably undesirable, since head-injury deaths are often due to infection, which could be related to malnutrition. Previous studies have suggested that alimentation with nonglucogenic (not converted to glucose in the body) energy substrates, such as ketone bodies, may have a less detrimental effect on neurological recovery from ischemia than alimentation with glucose Peek et al., "Ketone precursors as nutritional substrates may improve neurological outcome following ischemia", Journal of Neurotrauma, 1989 6:205-206.

Considering the negatives associated with fasting, there is a need for a nutritional product which will provide nutritional support after injury, yet not exaggerate the hyperglycemic response after injury. A nutritional product in accordance with the present invention: (a) is very low in, preferably free of, carbohydrate; (b) contains a lipid blend formulated to minimize the hypermetabolic response and reduce the frequency of ischemic events after severe head injury; and (c) an antioxidant system that restores antioxidant status in a head trauma patient and prevents or minimizes peroxidation of highly unsaturated fatty acids in the lipid blend.

DESCRIPTION OF THE PRIOR ART

U.S. Pat. No. 4,874,603 issued Oct. 17, 1989 to Fratzer relates to the desirability of administering vitamin E in combination with eicosapentanoic acid and docosahexanoic acid.

U.S. Pat. No. 4,263,286 issued Apr. 21, 1981 to Nakajima et al. relates to the administration of lecithin for treating consciousness disorder and perception and movement disorder.

Published reports have observed that the administration of large amounts of glucose just prior to episodes of cerebral ischemia accentuates post-ischemic brain dysfunction. "Deleterious Effect of Glucose Pretreatment on Recovery from Diffuse Cerebral Ischemia in the Cat", Ginsberg et al., STROKE, Vol. II, No. 4 (1980) pp. 347-354; and "Clinical restitution following cerebral ischemia in hypo-,normo- and hyperglycemic rats", Siemkowicz et al., ACTA NEUROLOGICA SCANDINAVICA, 58:1-8 (1978). Another publication indicates that nutritional supplementation with ketone precursors may improve neurological recovery following ischemia by providing substrates for energy metabolism without the deleterious effects associates with anaerobic glycolysis. "Ketone Precoursers as Nutritional Substrates May Improve Neurological Outcome Following Ischemia", Peek et al., JOURNAL OF NEUROTRAUMA, 6:205-206 (1989).

It has been hypothesized that the damaging effects on the brain of high serum glucose at the time of circulatory arrest are due to accumulation of lacatate in high concentration in brain tissue. "Effects of Serum Glucose Concentration on Brain Response to Circulatory Arrest", Meyers et al., JOURNAL OF NEUROPATHOLOGY AND EXPERIMENTAL NEUROLOGY, 35:301 (1976). It has also been concluded that a high degree of tactic acidosis during brain ischemia impairs postischemic recovery. "Brain Lactic Acidosis and Ischemic Cell Damage: 1 Biochemistry and Neurophysiology", Rehncrona et al., JOURNAL OF CEREBRAL BLOOD FLOW AND METABOLISM, 1:297-311 (1981).

There is a published study which concluded that major injury significantly alters carbohydrate metabolism. "Carbohydrate metabolism in man: Effect of elective operations and major injury", Long et al., JOURNAL OF APPLIED PHYSIOLOGY, Vol. 31, No. 1, June 1971, pp 110-116.

BRIEF DESCRIPTION OF THE DRAWINGS

To aquaint persons skilled in the art with the principles of the invention, a presently preferred embodiment illustrative of the best mode now comtemplated for the practice of the invention is described herein making reference to the attached drawings forming a part of the specification and in which drawings.

DETAILED DESCRIPTION OF THE INVENTION

Published experimental studies in models of cerebral hypoxia/ischemia have demonstrated a reduced central nervous system lactic acidosis and significant protective effects when 1,3-butanediol is administered intravenously prior to the ischemic event. It is not clear whether the protective effect is due to the 1,3-butanediol or to the ketone body metabolites.

1,3-Butanediol, an alcohol which is converted to $\beta$-hydroxybutyrate by the liver, was chosen for evaluation as one source of nonprotein calories. Although the intake of large doses of 1,3-butanediol has been demonstrated in animal studies to cause intoxication, no significant toxicity has been found with chronic administration of lower doses. Published studies of normal adults have shown that supplying 1,3-butanediol as 10% of the total caloric intake results in reduced nitrogen loss, decreased blood glucose, and increased $\beta$-hydroxybutyrate concentration.

The short chain fatty acids, acetate and butyrate, were chosen as the other nonprotein calorie source. The liver may utilize these short chain fatty acids for long-chain fatty acid synthesis and can convert butyrate and acetate into ketone bodies. In addition, these short chain fatty acids can be metabolized to $CO_2$ via the tricarboxylic acid cycle. Experimental studies in hypermetabolic animals with femoral fractures have demonstrated that acetate, supplied by infusion of monoacetin, is metabolized as efficiently as glucose, and has the advantage of not producing hyperglycemia. Maizet al., "Monoacetoacetin and protein metabolism during parenteral nutrition in burned rats." Journal of Biochemistry 1985; 226:43-50. Birkhanhan, et al "The influence of ketosis on the metabolic response to skeletal trauma", Journal of Surgical Research 1988; 44:160-165. The effect of short chain fatty acids on neurological recovery from ischemia has not been well-studied, but one report suggested that triacetin given intravenously, prior to spinal cord ischemia did not alter outcome. Peek, et al. "Ketone precursors as nutritional substrates may improve neurological outcome following ischemia", Journal of Neurotrauma 1989; 6:205-6.

The hypermetabolic response to severe head injury also is clinically characterized by an increased resting energy expenditure, accelerated wholebody protein turnover and negative nitrogen balance. These metabolic changes are thought to be mediated by elevations in circulating catecholamines, cortisol, glucagon and other mediators of the stress response resulting in net protein catabolism and the loss of lean body mass. Eicosanoids (prostaglandins, prostacyclins, thromboxanes, leukotrienes) derived from arachidonic acid, which is an integral component of the mammalian cell membrane, are important mediators of the vascular component of the hypermetabolic response. Attempts to reduce particularly thromboxane $A_2$ production by providing an essential fatty acid deficient diet, by reducing arachidonic acid availability or by the use of enzymatic blockade of eicosanoid metabolism through cyclooxygenase or thromboxane synthetase inhibition, has generally improved outcome in animal models of hypermetabolism if given as a pretreatment. However, there are serious and probably limiting side effects as a consequence of such broad inhibition of many other vital functions in man.

The investigation of different types of lipid sources has lead to the realization that specific n-6 and n-3 fatty acids can modify the normal host response to metabolic injury. An alternative means by which to influence eicosanoid metabolism and thereby modify the hypermetabolic response has been the provision of lipids containing eicosapentaenoic (EPA) acid found principally in fish oils and gamma-linolenic acid (GLA) from borage oil. These fatty acids favorably alter eicosanoid metabolism. The total amount of eicosanoids released in response to stress are decreased by these two fatty acids, and the type of eicosanoids released is also changed. GLA serves as a precursor for monoenoic eicosanoids which have antiinflammatory potential. GLA is efficiently and quickly elongated to dihomo-gammalinolenic acid which competes with arachidonic acid for cyclooxygenase, and may reduce production of series-2 prostaglandins such as $PGE_2$ with immunosuppressive and pro-inflammatory properties. EPA serves as a precursor for trienoic prostaglandins and series-5 leukotrienes which maintain vasodilator function with minimal vasoconstrictor and platelet aggregatory function. Therefore the net effect of combining EPA and GLA is a change in the hemostatic balance of eicosanoids to strongly favor an antiinflammatory vasodilatory state with less platelet aggregation than would not be effectively achieved by EPA alone.

Alteration of eicosanoid metabolism by these dietary means can thus downregulate both prostaglandin and leukotriene metabolism, unlike systemic inhibition with pharmacologic drugs. The use of fatty acids such as linoleic (n-6) and $\alpha$-linolenic (n-3) acids are not likely to favorably influence eicosanoid metabolism following severe injury, because of the slow conversion by delta-6-desaturase of linoleic acid to GLA and $\alpha$-linolenic acid to stearidonic acid. Thus one is not likely to achieve the benefits claimed for fish and borage oils containing EPA and GLA respectively, by using corn and canola oils. A final mechanism by which fish oils may alter the inflammatory response is through reductions in monokine production following endotoxin stimulation. It has been demonstrated that fish oil supplementation of a normal diet in healthy volunteers could reduce the physiologic effects of endotoxin. Interleukin 1 and tumor necrosis factor production was reduced in endotoxin stimulation in their monocutes isolated from these individuals.

EXPERIMENT I

In the first experiment the objective was to evaluate the effect of alimentation with five experimental diets, in which a major portion of the carbohydrate calories were replaced by nonglucogenic substrates, such as short-chain fatty acids, lipid (corn oil) or 1,3-butanediol. The size of the infarction caused by temporary occlusion of the middle cerebral artery was compared to the injury produced when animals were fed a conventional enteral formula (high carbohydrate, negative control) and starvation (positive control). The experimental diets are presented in Table 1, in which diet number one is a control diet. In these diets over 30% of the dietary carbohydrate calories were replaced by nonglucogenic substrates.

TABLE 1

EXPERIMENTAL DIETS
CALORIC DISTRIBUTION (all values in %)

| INGREDIENTS | DIET-1 | DIET-2 | DIET-3 | DIET-4 | DIET-5 | DIET-6 |
|---|---|---|---|---|---|---|
| Protein | 16.8 | 17.1 | 17.3 | 16.9 | 16.9 | 16.6 |
| Carbohydrates | 52.0 | 20.4 | 23.6 | 21.7 | 22.8 | 21.9 |
| LCT* | 31.2 | 15.6 | 15.7 | 15.0 | 15.9 | 61.5 |
| MCT* | 0 | 15.6 | 14.3 | 14.9 | 14.0 | 0 |
| Triactin | 0 | 0 | 13.4 | 31.5 | 0 | 0 |
| Tributyrin | 0 | 0 | 15.8 | 0 | 30.4 | 0 |
| 1,3-Butanediol | 0 | 31.2 | 0 | 0 | 0 | 0 |

*LCT = long chain triglycerides.
*MCT = medium chain triglyceride.

The control diet (diet 1) was similar to commercially available nasogastric feedings, with about 51.5% of the calories contributed by carbohydrates, and about 17% by protein. The experimental diets all had the same protein-carbohydrate base, with about 17% protein and about 21% carbohydrate calories. About 30% of the calories in diets 2-5 were from long-chain and medium-chain triglycerides with the remaining (about 32%) of the calories either from 1,3-butanediol (diet 2), triacetin and tributyrin (diet 3), triacetin (diet 4), or tributyrin (diet 5). Triacetin was found to be unstable in a liquid product, therefore, triacetin was added to the product just prior to feeding. About 62% of the calories in diet 6 were from long chain triglycerides. The caloric density of all of the diets was about 1.5 kcal/ml.

Long Evans rats weighing 300 gm±25 gm were used in this study. The rats were randomly assigned to one of seven treatment groups. Six of the groups were fed one of the experimental diets shown in Table 1 for 12 hours prior to an ischemia study. A seventh group was fasted for 24 hours prior to an ischemia study. All of the experimental diets were well tolerated by the rats.

On the day prior to the ischemia study, the rats were anesthetized. A polyethylene tube was tunneled under the skin from the right nostril to the mid-scapular region of the back. The end of the tube was inserted through the right nostril, postioning the tip in the stomach. The tube was then securely sutured in place. After the animals had fully awakened, the assigned diet was started as a continuous nasogastric infusion at 110 kcal/(kgBW)$^{.75}$/day, a rate which would replace 100% of their caloric expenditure over 24 hours. In preliminary studies, it was determined that plasma glucose concentration reached a steady state within 3 hours of starting the infusion. The animals were fed for 12 hours prior to the ischemia study in order to assure steady state conditions.

On the day of the ischemia study, the rats were anesthetized. The rat's rectal temperature was monitored continuously and maintained at 37.5°±5° C. with a heating pad and/or lamp. The right femoral artery was cannulated for monitoring arterial blood pressure and heart rate, and for obtaining blood samples for glucose and blood gases. A ventral midline cervical incision was made and both common carotid arteries were carefully isolated. Care was taken to avoid injuring nerves adjacent to the arteries. A 1.5 cm incision was made at the midpoint between the right eye and ear. The temporalis muscle was separated in the plane of its fiber bundles and retracted to expose the zygoma and squamosal bone. Using microsurgical technique, a burr holes, 2 mm in diameter, was made with a dental drill 1 mm rostral to the anterior junction of the zygoma and squamosal bone. Care was taken to avoid thermal or physical injury to the cortex during preparation of the burr hole. The dura was carefully pierced with a #11 scalpel blade, exposing the middle cerebral artery. Immediately prior to producing the experimental ischemia, a 1 mL blood sample was obtained through the arterial catheter for measurement of arterial blood glucose which is presented in Table 2.

TABLE 2

ARTERIAL CONCENTRATIONS OF GLUCOSE
(mmoL/L) PRIOR TO ISCHEMIA

| | FASTED | DIET-1 | DIET-2 | DIET-3 | DIET-4 | DIET-5 | DIET 6 |
|---|---|---|---|---|---|---|---|
| # of rats | 15 | 15 | 8 | 8 | 8 | 8 | 7 |
| Glucose | 6.38 ± 1.11 | 9.05 ± 1.39* | 7.83 ± 1.33*+ | 8.83 ± 1.22* | 10.05 ± 1.89* | 9.44 ± 1.44* | 8.66 ± 0.83* |

* = different from fasted ($p < .05$)
+ = different from diet 1 ($p < .05$)

Plasma glucose concentration was increased by the diets (Table 2). The mean glucose concentration prior to ischemia in the fasted animals was 6.38 ±1.11 mmol/L (115±20 mg/dL). The mean glucose concentration with the normal control diet (diet 1), which contained the most carbohydrate calories was 9.05±1.39 mmol/ml (163±25 mg/dL). The lowest preischemia glucose concentration among the experimental diets was in the 1,3-butanediol (diet 2) group, averaging 7.83±1.33 mmoL/L (141±mg/dL). The preischemia plasma glucose concentration with diets 3–6 was not significantly different from the normal control diet (diet 1).

In order to cause an infarct, the middle cerebral artery was temporarily occluded by slipping a curved 100 micron diameter microvascular needle under the artery and gently lifting the vessel. Complete occlusion of the vessel was visually confirmed. At the same time, both common carotid arteries were clipped with traumatic aneurysm clips. After 45 minutes, the clips and the needle were removed and reperfusion was observed in all animals. The arterial catheter was removed, all surgical wounds were sutured, and the animals were allowed to awaken from anesthesia. To minimize the risk of aspiration during the ischemia period, the nasogastric feedings were stopped just before occluding the middle cerebral artery.

The infarct volume in the right middle cerebral artery (MCA) territory was measured morphometrically, using 2,3,5-triphenyltetrazolium chloride (TTC). In previous studies with this model, the size of the cortical infarction in the MCA territory progressively increased up to 6 hours after ischemia, and remained unchanged from 6 to 72 hours. Yip, P. K., He, Y. Y., Hsu, C. Y. et al: "Effect se on infarct size in focal cerebral ischemia-reperfusion", Neurology 1991; 41:899–905. Twenty-four hours after the ischemia period, the rats were deeply anesthetized with ketamine and xylazine and were perfused via the left ventricle with 200 mL 0.9% saline. The brain was removed, cooled in iced saline for 5 minutes, and dissected in the coronal plan at 2 mm intervals using a brain slicer. The brain slices were incubated in 2% TTC in phosphate-buffered saline at 37° C. and then stored in 10% neutral-buffered formalin for morphometric studies. The cross-sectional area of infarction on both the anterior and posterior surfaces of each of eight brain slices was measured using a computerized image analysis system. The total infarct volumes which are presented in FIG. 1 were derived from the sum of the average infarct volume from each slice.

Figure 1:
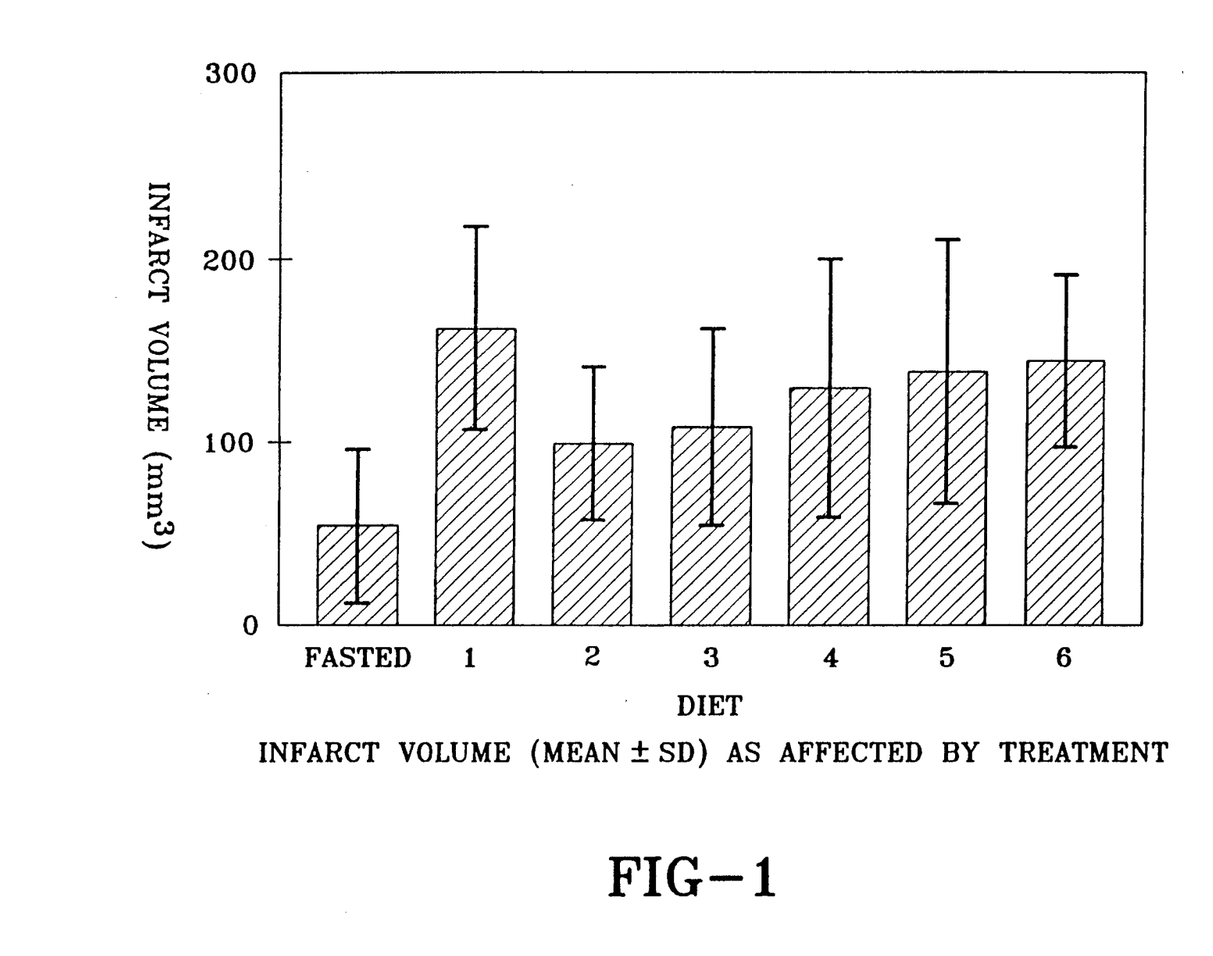
FIGS. 1 and 2 are graphs presenting infarct volume as a function of diet.

The volume of the infarcted tissue was significantly related to the diet (FIG. 1). The smallest infarcts were obtained in the fasted group, averaging $52.9 \pm 43.4$ mm$^3$. The largest infarcts were seen in the normal control diet (diet 1), averaging $162.1 \pm 55.8$ mm$^3$. Of the experimental diets, the smallest infarct volumes occurred in the 1,3-butanediol (diet 2) group, with a mean of $98.3 \pm 41.1$ mm$^3$ and in the triacetin/tributyrin (diet 3) group, with a mean of $105.4 \pm 52.6$ mm$^3$. There was a positive correlation between the preischemia plasma glucose concentration (Table 2) and the volume of an infarct (FIG. 1).

Experiment I demonstrates that not only the nutritional state (fasted vs fed) but also the content of the diet, can alter recovery from cerebral ischemia. The source of the nonprotein calories can alter both the blood glucose concentration and the size of the resulting cerebral infarction. It was decided at this point to attempt to develop a diet containing ingredients such as 1,3-butanediol, triacetin, or tributyrin, which would meet the nutritional requirements of patients without adversely affecting neurological recovery from temporary cerebral ischemia.

EXPERIMENT II

Based on data collected in Experiment I a decision was made to evaluate six additional experimental diets that replace carbohydrate and/or protein with various combinations of long-chain and medium-chain triglycerides, short chain triglycerides (triacetin and tributyrin), or 1,3-butanediol. The results of the proximate, mineral and vitamin assays for the seven diets used in this experiment are presented in Table 3. Table 4 summarizes the caloric distribution of the seven diets using the following caloric densities: 4.0 kcal/g for protein and carbohydrate, 8.3 kcal/g for medium chain triglycerides (MCT), 9.0 kcal/g for long chain triglycerides (LCT) and 6.0 kcal/g for 1,3-butanediol, 4.6 kcal/g for triacetin, and 6.49 kcal/g for tributyrin. Calories from carbohydrates were based on the amount of carbohydrate added. Results of physical stability studies for the seven products, conducted about four days after the products were manufactured, are presented in Table 5.

TABLE 3

HEAD TRAUMA ANIMAL STUDY PRODUCTS
PROXIMATE, VITAMIN AND MINERAL RESULTS

|  | DIET-7 | DIET-8[a] TRIACETIN | DIET-9 | DIET-10 | DIET-11 | DIET-12 | DIET-13 |
|---|---|---|---|---|---|---|---|
| Total Solids, g/100 g | 30.81 | 24.81 | 24.4 | 26.9 | — | — | 20.99 |
| Protein, g/100 g | 6.21 | 6.08 | 6.09 | 6.05 | — | — | 8.88 |
| Fat (MCT + LCT), g/100 g | 4.94 | 7.88 | 8.42 | 6.70 | 11.22 | — | 6.46 |
| Tributyrin, g/100 g | — | 3.47 | — | — | — | — | — |
| Triacetin, g/100 g | — | 5.14 | — | — | — | — | — |
| 1,3-Butanediol, g/100 g | — | — | 7.46 | 7.54 | 7.77 | 25.3 | 7.70 |
| Ash, g/100 g | 0.625 | — | 0.607 | 0.598 | — | — | 0.574 |
| Density, g/ml | 1.09696 | — | 1.01675 | 1.033325 | 1.00285 | 1.01447 | 1.04162 |
| Carbohydrate, g/100 g (amount added) | 18.32 | — | — | 3.56 | — | — | 3.58 |
| Calcium, mg/100 g | 22.5 | 22.0 | 22.3 | 22.8 | 24.8 | 25.9 | 23.4 |
| Sodium, mg/100 g | 109 | 112 | 113 | 113 | 175 | 116 | 108 |
| Potassium, mg/100 g | 141 | 141 | 141 | 134 | 68.7 | 76.9 | 140 |
| Magnesium, mg/100 g | 1.39 | 1.12 | 1.13 | 1.21 | 1.08 | 1.33 | 0.9888 |
| Phosphorus, mg/100 g | 76.7 | 74.9 | 76.0 | 76.2 | 74.0 | 80.2 | 76.0 |
| Chloride, mg/100 g | 39.3 | 35.0 | 36.4 | 38.2 | 32.44 | 32.58 | 40.05 |
| Zinc, mg/100 g | 2.60 | 2.60 | 2.61 | 2.61 | 2.42 | 2.62 | 2.73 |
| Iron, mg/100 g | 1.92 | 1.66 | 1.67 | 1.84 | 1.91 | 2.19 | 1.85 |
| Copper, mg/100 g | 0.196 | 0.194 | 0.184 | 0.199 | 0.149 | 0.250 | 0.188 |
| Manganese, mg/100 g | 0.437 | 0.454 | 0.462 | 0.459 | 0.493 | 0.571 | 0.454 |
| Vitamin B[1], mg/kg | 6.02 | 5.61 | 5.45 | 5.72 | 4.60 | 4.38 | 5.37 |
| Vitamin C, mg/kg | 632 | 567 | 617 | 594 | 640 | 672 | 630 |
| Pyridoxine, mg/kg | 5.90 | 5.50 | 5.95 | 5.92 | 6.44 | 6.58 | 5.45 |
| Vitamin A, IU/l | 8050 | 8072 | 8130 | 6400 | 7840 | 5460 | 7180 |

TABLE 3-continued

HEAD TRAUMA ANIMAL STUDY PRODUCTS
PROXIMATE, VITAMIN AND MINERAL RESULTS

|  | DIET-7 | DIET-8[a] TRIACETIN | DIET-9 | DIET-10 | DIET-11 | DIET-12 | DIET-13 |
|---|---|---|---|---|---|---|---|
| Vitamin E, IU/l | 56.1 | 55.5 | 54.5 | 45.3 | 50.0 | 43.9 | 51.6 |

[a]Calculated based on 5.42 grams of Triacetin added to 100 grams of DIET-8 module.

TABLE 4

HEAD TRAUMA ANIMAL STUDY PRODUCTS
CALORIC DISTRIBUTION
(All values in percent)

|  | DIET-7 | DIET-8[a] | DIET-9 | DIET-10 | DIET-11 | DIET-12 | DIET-13 |
|---|---|---|---|---|---|---|---|
| Protein | 17.4 | 17.6 | 17.2 | 17.1 | — | — | 24.8 |
| MCT | — | 26.3 | 25.6 | 20.4 | 33.7 | — | 16.5 |
| LCT | 31.2 | 22.8 | 25.6 | 20.4 | 33.8 | — | 16.5 |
| Tributyrin | — | 16.3 | — | — | — | — | — |
| Triacetin | — | 17.1 | — | — | — | — | — |
| 1,3-Butanediol- | — | — | 31.6 | 32.0 | 32.5 | 100 | 32.3 |
| Carbohydrate | 51.4 | — | — | 10.1 | — | — | — |
| 10.0 (amount added) |  |  |  |  |  |  |  |
| Total Kcal/L | 1564 | 1405 | 1442 | 1462 | 1439 | 1540 | 1491 |

[a]Caloric distribution after 5.42 g. of triacetin addition to 100 g. of module.

TABLE 5

HEAD TRAUMA ANIMAL STUDY PRODUCTS
4-DAY PHYSICAL STABILITY

|  | pH | VISCOSITY | GRAIN[a] | AGTRON[b] |
|---|---|---|---|---|
| DIET-7 | 6.46 | 21.0 | 1 | 45.3 |
| DIET-8 | 6.46 | 16.6 | 1 | 69.2 |
| DIET-9 | 6.47 | 11.9 | 1 | 62.1 |
| DIET-10 | 6.48 | 12.7 | 1 | 58.1 |
| DIET-11 | 5.59 | 74.6 | — | 74.0 |
| DIET-12 | 6.21 | 13.8 | — | 76.6 |
| DIET-13 | 6.46 | 52.1 | 1 | 53.4 |

[a]Grain is a qualitative descriptor of protein stability with a value of 1 being best and a value of 6 being worst.
[b]Agtron is a color scale measurement with a value of 1 being very dark and a value of 100 being white.

Long Evans rats weighing 300±25 gm were used in this experiment. A total of eight diets were involved. Seven of the groups were fed one of the diets shown in Table 3 for 12 hours prior to an ischemia study. The negative control group (diet 7) contained 14 animals. The remaining experimental groups (diets 8–13) contained 10 animals per treatment. A positive control group of 12 animals was fasted for 24 hours prior to the ischemia study. The negative control diet (diet 7) was similar to a commercially available nasogastric feeding, with 51.5% of the calories contributed by carbohydrates. The experimental diets contained varying amounts of protein and carbohydrate. Calories not provided by carbohydrate or protein were contributed by long-chain and medium-chain triglycerides, triacetin and tributyrin, and/or 1,3-butanediol. The caloric density of all diets was approximately 1.5 kcal/ml. All of the diets except diet 12 were well tolerated during the nasogastric infusion. Diet 12 caused signs of intoxication, an osmotic dieuresis, and hypotension, and resulted in a 50% mortality rate during the ischemia period.

Prior to the ischemic challenge a blood sample was obtained through the arterial catheter for measurement of plasma glucose (preischemia value). The rats were prepared for the ischemia study in substantially the same manner as described in Experiment I. The middle cerebral artery was temporarily occluded by slipping a 100 micron diameter microvascular needle under and gently lifting the vessel. As the same time, both common carotid arteries were clipped with traumatic aneurysm clips. After 60 minutes had elapsed, the clips and needle were removed and reperfusion was observed in all animals. A blood sample was obtained through the arterial catheter for measurement of plasma glucose, (post-ischemia value).

The arterial catheter was then removed, all surgical wounds were sutured closed, and the animals were allowed to awaken from anesthesia.

Figure 2:
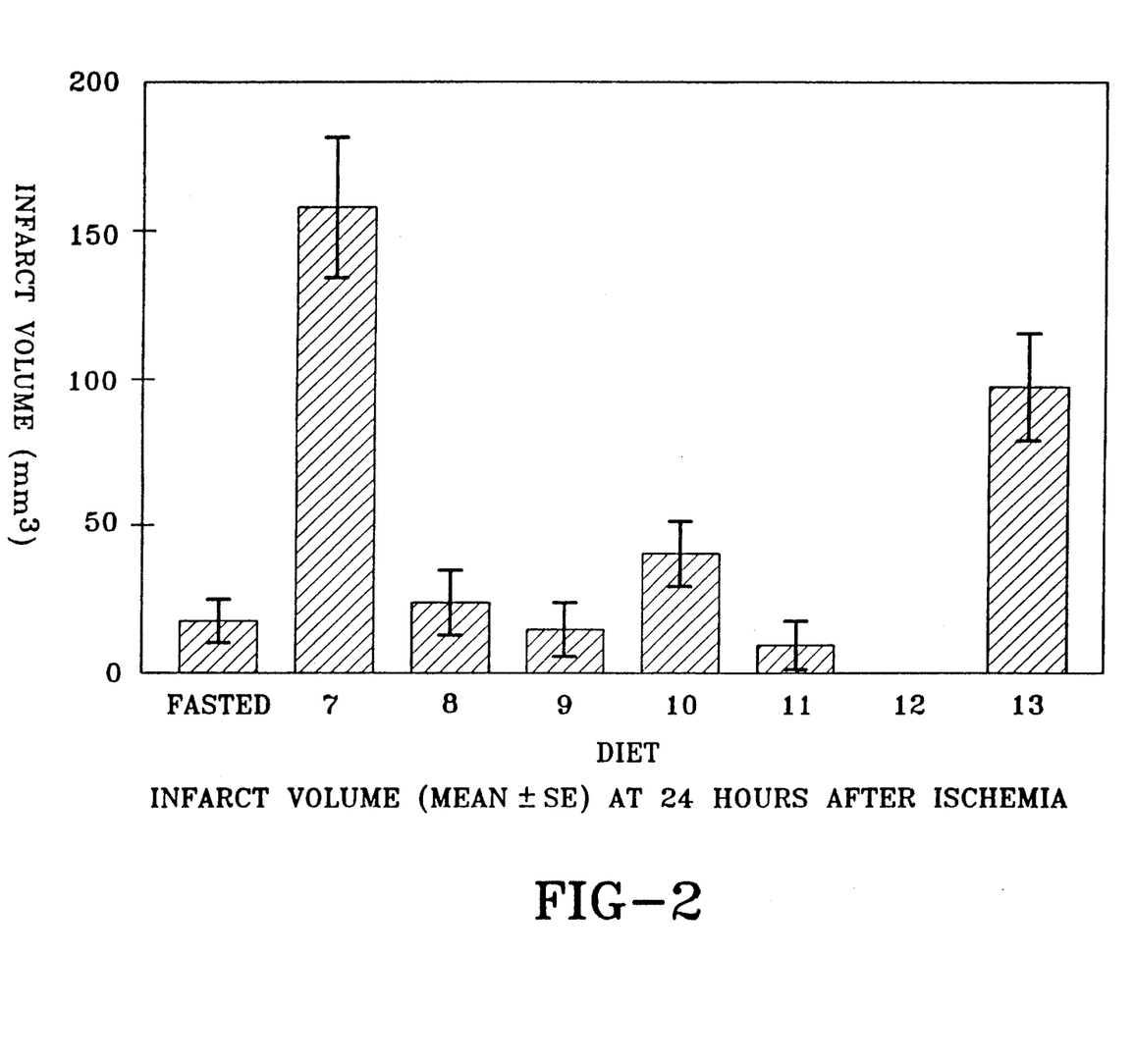

The infarct volumes were determined in the same manner described in Experiment I, and are presented in FIG. 2. Pre-ischemia and post-ischemia arterial concentrations of glucose are presented in Table 6.

TABLE 6

ARTERIAL CONCENTRATIONS OF ENERGY SUBSTRATES

|  | Fasted | Diet 7 | Diet 8 | Diet 9 | Diet 10 | Diet 11 | Diet 12 | Diet 13 |
|---|---|---|---|---|---|---|---|---|
| Number of Rats | 12 | 14 | 10 | 10 | 10 | 10 | 4 | 10 |
| Preischemia Value: |  |  |  |  |  |  |  |  |
| Glucose, mg/dL | 115 ± 10 | 223 ± 14* | 154 ± 9*+ | 150 ± 9*+ | 157 ± 10*+ | 105 ± 7+ | 74 ± 14*+ | 164 ± 9*+ |
| Postischemia Value: |  |  |  |  |  |  |  |  |
| Glucose, mg/dL | 131 ± 16 | 233 ± 24* | 178 ± 24 | 147 ± 12+ | 182 ± 19 | 105 ± 7+ | 97 ± 7+ | 166 ± 18+ |

* = different from fasted ($p < .05$)
+ = different from diet 7 ($p < .05$)

The preischemia plasma glucose concentrations (Table 6) were significantly related to the diet. The glucose concentration prior to ischemia was highest in the normal control diet (diet 7). The glucose concentration was lowest in the diets that did not contain carbohydrates or protein (diets 11 and 12) and was intermediate in the remaining diets (diets 8, 9, 10 and 13). The volume of the infarcted tissue was significantly related to diet (FIG. 2). Diets 7 and 13 resulted in a mean infarct volume significantly greater than fasting and diets 8-12. Diets 8-12 were not significantly different from fasting with regard to infarct volume. In the 4 animals surviving diet 12 (100% of calories from 1,3-butanediol) no infarct was detected. Another interesting point involves diet 10 and 13. The diets differ in the percent of calories from protein (diet 10, 17%; diet 13, 25%). Infarct volume was greater in diet 13 compared to diet 10. High levels of protein increase infarct volume. The negative effect of protein may be related to its glucogenic effect. There was a strong, direct relationship between both preischemia ($r=0.67$, $P<0.001$) and postischemia ($r=0.74$, $P<0.001$) plasma glucose concentration and size of the infarction.

Considering the promising results obtained in Experiments I and II, it was apparent that the development of nutritional product for patients suffering from neurological injury is possible. Experimental products containing 1,3-butanediol and a blend of triacetin and tributyrin have resulted in a reduction in infarction caused by temporary occlusion of the middle cerebral artery in a rat model compared to a conventional enteral formula (high carbohydrate). In fact, these products were as effective as fasting. However, certain problems are associated with the alternative energy substrates, 1,3-butanediol, triacetin and tributyrin. First, the short chain triglycerides, particularly triacetin, are unstable in a liquid enteral product. If the product is made in a powdered form, to be reconstituted with water at the time of consumption this problem will not occur. Such a powdered product is considered to be within the scope of the present invention. The problem with triacetin is so severe at the present time that the commercialization of a liquid product containing this ingredient is highly unlikely. However; it is understood that a liquid nutritional product containing triacetin is within the scope of the present invention.

Second there are regulatory issues associated with the alternative energy substrates. None of these alternative energy substrates are generally regarded as safe (GRAS) at the intended level of use. Also, upon review of the available information on 1,3-butanediol it was concluded that additional toxicological studies would be required before the initiation of any clinical studies involving 1,3-butanediol. The processing and/or regulatory concerns associated with the alternative energy substrates will preclude their use in liquid enteral products at this time. Nevertheless, the significant correlation between infarct volume and plasma glucose noted in Experiments I and II is critical because there is a positive correlation between the level of carbohydrate in the diet and infarct volume. Also, there is some indication in Experiment II that excessive levels of protein may increase infarct volume. Considering this information, it was possible to develop products which should be as effective as the experimental products containing the alternative energy substrates or fasting simply by utilizing a reasonable level of protein (17-20% of calories) and removing all carbohydrate and replacing the calories with a blend of medium and long chain triglycerides.

PREFERRED EMBODIMENTS

It was felt that additional benefits can be obtained by including in the nutritional product of the present invention nutrients which exhibit antioxidant activity in a patient with a severe head injury.

An oxygen-free radical contains one or more unpaired electrons, an unpaired electron being one that is alone in an orbital. Because electrons are stable when paired together in orbitals, radicals are more reactive than non-radical species. Radicals can react with other molecules in a number of ways. The interest in the role of free radicals and hydrogen peroxide in human disease has grown rapidly.

It is widely recognized that many critical illnesses may involve oxygen radical pathophysiology. Oxyradicals can devastate all four major classes of macromolecules composing living matter, and a variety of mechanisms exist for the generation of these toxic species, especially in the critically ill patient.

The hydroxyl radical is the most reactive radical species, in that it can attack and damage almost every molecule found in living cells. In fact, the formation of hydroxyl radicals is the major mechanism by which malignant cells are killed during radiotherapy. Lipid peroxidation is a well characterized biologic damage caused by the hydroxyl radical. It is the highly unsaturated fatty acids which are the most susceptible since the hydroxyl radical preferentially attacks fatty acids with several double bonds.

A decision was made to fortify the nutritional product of the present invention with quantities of vitamins C and E at levels that meet or exceed the NAS/NRC RDA's for these nutrients because they are reported in the literature as having desirable antioxidant properties in humans. Selenium, beta-carotene, molybdenum and taurine are also believed to exhibit desirable antioxidant activities. It is believed that severe injury of any sort may be aggravated by oxidation of lipids at a cellular level.

Vitamin C is a hydrophyllic vitamin with well known antioxidant properties. Vitamin E is a mixture of four lipid-soluble tocopherols. Alpha-tocopherol is the most active of the four tocopherols at trapping peroxyl radicals. The vitamin E radical is fairly stable due to delocalization of the unpaired electron. The functional interrelation between vitamin E and other micronutrients, notably selenium and vitamin C, has long been recognized. For example, several symptoms of vitamin E deficiency are preventable by selenium, and the severity of these symptoms is linked to the nutritional status of selenium. The synergistic effect of vitamin C on vitamin E can be attributed to vitamin C's antioxidant properties or to vitamin C's role in the regeneration of vitamin E. It has long been established that the requirement for vitamin E is related to the amount of polyunsaturated fat in the diet. It is understood that a liquid nutritional product in accordance with the broad aspect of the invention may contain one or more of the nutrients selected from the group consisting of beta-carotene, vitamin E, vitamin C, taurine and ultratrace minerals such as molybdenum and selenium.

It is further considered to be within the scope of the present invention to incorporate a source of dietary fiber in the enteral nutritional product, for example the dietary fiber system taught in U.S. Pat. No. 5,085,883.

Based upon the results of the foregoing experiments four nutritional products in accordance with the present invention have been manufactured. The Bill of Materials for manufacturing a 200 pound batch of each of these four products is presented in Table 7.

TABLE 7

HEAD TRAUMA FORMULATIONS
BILL OF MATERIALS FOR 200 LB BATCHES

| INGREDIENT | DIET-14 | DIET-15 | DIET-16 | DIET-17 |
|---|---|---|---|---|
| MCT Oil, lbs | 5.80 | 5.80 | 6.58 | 3.34 |
| *Marine Oil, lbs | 2.46 | — | — | — |
| Canola Oil, lbs | 6.62 | 9.60 | 10.9 | 5.50 |
| Borage Oil, lbs | 2.46 | — | — | — |
| 1,3-Butanediol, lbs | — | — | — | 15.36 |
| High Oleic Safflower Oil, lbs | 5.88 | 7.84 | 8.90 | 4.48 |
| Soy Lecithin, g | 552 | 554 | 626 | 317 |
| Acid Casein, lbs | 20.3 | 20.3 | 14.2 | 20.3 |
| 20% Sodium Hydroxide, g | 955 | 955 | 665 | 955 |
| Potassium Citrate, g | 223 | 223 | 155 | 223 |
| Magnesium Phosphate, g | 185 | 185 | 185 | 185 |
| Calcium Carbonate, g | 231 | 231 | 133 | 231 |
| Magnesium Chloride, g | 92.5 | 92.5 | 92.6 | 92.6 |
| Calcium Phosphate Tribasic, g | 17.9 | 17.9 | 122 | 17.7 |
| Potassium Chloride, g | 204 | 204 | 207 | 204 |
| Sodium Citrate, g | 19.7 | 19.7 | 163 | 19.9 |
| Mineral Premix, g | 28.3 | 28.3 | 28.3 | 28.3 |
| Zinc (as zinc sulfate), g | 2.35 | 2.35 | 2.35 | 2.35 |
| Iron (as ferrous sulfate), g | 1.79 | 1.79 | 1.79 | 1.79 |
| Manganese (as Mn Sulfate), g | 0.50 | 0.50 | 0.50 | 0.50 |
| Copper (as copper sulfate), g | 0.21 | 0.21 | 0.21 | 0.21 |
| Selenium (as Na selenite), mg | 7.74 | 7.74 | 7.74 | 7.74 |
| Chromium (as Cr chloride), mg | 8.47 | 8.47 | 8.47 | 8.47 |
| Molybdeum (as Na Molybdate), mg | 16.6 | 16.6 | 16.6 | 16.6 |
| Sucrose (carrier) | QS | QS | QS | QS |
| Potassium Iodide, mg | 21.8 | 21.8 | 21.8 | 21.8 |
| Oil Soluble Vitamin Premix, g | 6.94 | 6.94 | 6.94 | 6.94 |
| Vitamin A palmitate, IU | $7.7 \times 10^5$ | $7.7 \times 10^5$ | $7.7 \times 10^5$ | $7.7 \times 10^5$ |
| Vitamin D, IU | $4.5 \times 10^4$ | $4.5 \times 10^4$ | $4.5 \times 10^4$ | $4.5 \times 10^4$ |
| dl-alpha tocopheryl acetate, IU | $5.1 \times 10^3$ | $5.1 \times 10^3$ | $5.1 \times 10^3$ | $5.1 \times 10^3$ |
| phylloquinone (vit. K), mg | 9.37 | 9.37 | 9.37 | 9.37 |
| coconut oil carrier | Q.S. | Q.S. | Q.S. | Q.S. |
| dl-alpha tocopheryl acetate, g | 23.1 | 23.1 | 23.1 | 23.1 |
| Ascorbic Acid, g | 60 | 60 | 60 | 60 |
| Water Soluble Vitamin Premix, g | 12.8 | 12.8 | 12.8 | 12.8 |
| Niacinamide, g | 4.80 | 4.80 | 4.80 | 4.80 |
| d-calcium Pantothenate, g | 3.11 | 3.11 | 3.11 | 3.11 |
| Pyridoxine Hydrochloride, g | 0.76 | 0.76 | 0.76 | 0.76 |
| Thiamin Hydrochloride, g | 0.79 | 0.79 | 0.79 | 0.79 |
| Riboflavin, g | 0.62 | 0.62 | 0.62 | 0.62 |
| Folic Acid, g | 0.11 | 0.11 | 0.11 | 0.11 |
| Biotin, g | 0.094 | 0.094 | 0.094 | 0.094 |
| Cyanocobalamin, mg | 2.12 | 2.12 | 2.12 | 2.12 |
| Dextrose carrier | Q.S. | Q.S. | Q.S. | Q.S. |
| Taurine, g | 17.6 | 17.6 | 17.6 | 17.6 |
| Carnitine, g | 8.8 | 8.8 | 8.8 | 8.8 |
| Choline Chloride, g | 42.0 | 42.0 | 42.0 | 42.0 |
| Ingredient Water, Lbs | 151 | 151 | 154 | 146 |

*Refined Sardine Oil w/high concentrations of omega-3 fatty acids(EPA/DHA: 28:12). MCT may be in form of fractionated coconut oil.

In each instance the nutritional products of the present invention were manufactured according to the following procedure.

A protein-in-water slurry is prepared by following a procedure described in U.S. Pat. No. 4,880,912. That is to say, an appropriate amount of water to make a slurry containing about 14% total solids is placed into a suitable tank and heated to a temperature of about 150°–170° F. Potassium citrate is then added to the water and held for 1 minute. The pH of the solution is then determined followed by the addition of the acid casein. The required amount of 20% sodium hydroxide solution (prepared in advance) is then added to the slurry. The protein-in-water slurry is then recirculated and held for eight minutes when the pH is once again determined. The pH specification is 6.4 to 7.1. If the pH is below 6.4, additional sodium hydroxide is added. The slurry is held at a temperature of 145°–155° F. with agitation. This temperature is critical. The manufacturing process is set forth in greater detail in the following paragraphs.

A mineral slurry is prepared by placing the appropriate amount of water to make a slurry containing 10 to 20% total solids in a suitable tank and heating the water to a temperature of about 140°–160° F. The magnesium chloride, potassium chloride, sodium citrate, potassium iodide, and mineral premix are then added. The slurry is agitated until a clear green solution is produced. The calcium phosphate tribasic, calcium carbonate, and magnesium phosphate are then added with agitation. The slurry recirculated and maintained at a temperature of 140°–160° F.

An oil blend is prepared by combining the appropriate oils, marine (refined sardine), or borage, or canola, or high oleic safflower, or MCT oil in a blend tank with agitation and heating the blend to 90°–110° F. The required amount of emulsifier, soy lecithin, is added to the heated oil. The oil soluble vitamins are added next via a premix and individual vitamin E concentrate. Vitamin containers are rinsed with a small amount of oil to assure complete transfer.

The protein in water slurry, the mineral slurry, and the oil blend are combined with agitation to yield a blend having 25 to 26% total solids by weight. The blend, held at a temperature of 130°-150° F. should be in the pH range of 6.45-6.90. If a pH adjustment is needed, 1N KOH or 1N citric acid is added.

The blend is emulsified, homogenized in a two stage homogenizer at 3900-4100/400-600 psig, then high temperature short time processed (160°-175° F.) for 16 seconds. The processed blend is then cooled to about 40° F.

A solution of vitamins is prepared by first adding a vitamin premix to an appropriate amount of 50°-110° F. water to make a 4% total solids solution. The ascorbic acid, choline chloride, carnitine, taurine, and 45% KOH are added to the solution with agitation. The blend should be in the pH range of 6.0-10.0 and is adjusted with 45% KOH if the pH is below 6.0. The vitamin solution is then added to the blend.

Additional water is added to the blend to reach a final total solids in the blend of 23%-26%.

The pH of the complete blend is adjusted with 1N KOH, placed in suitable containers such as 8 oz. metal cans and terminally sterilized. Alternatively, the manufacturing process may be adapted to accommodate aseptic packaging of the product in suitable containers. The finished product of the preferred embodiment is a ready-to-serve liquid.

The composition and characteristics of the lipid blends employed in these preferred embodiments are presented in Tables 8, 9 and 10.

TABLE 8

OIL BLENDS OF PREFERRED EMBODIMENTS (BY % WEIGHT)

| INGREDIENT | DIET-14 | DIETS 15, 16 & 17 |
|---|---|---|
| Canola Oil | 27 | 39 |
| Medium Chain Triglycerides (MCT) | 24 | 24 |
| High Oleic Safflower Oil | 24 | 32 |
| Soy Lecithin | 5 | 5 |
| Borage Oil | 10 | — |
| Fish Oil | 10 | — |

TABLE 9

FATTY ACID PROFILES OF OIL BLENDS OF PREFERRED EMBODIMENTS (BY % WEIGHT)

| INGREDIENT | DIET-14 | DIETS 15, 16 & 17 |
|---|---|---|
| CAPROIC (6:0) | 0.02 | 0.02 |
| CAPYRLIC (8:0) | 15.36 | 15.36 |
| CAPRIC (10:0) | 8.52 | 8.52 |
| LAURIC (12:0) | 0.11 | 0.10 |
| MYRISTIC (14:0) | 0.70 | 0.07 |
| PALMITIC (16:0) | 5.06 | 4.08 |
| PALMITOLEIC (16:1n7) | 1.13 | 0.11 |
| STEARIC (18:0) | 1.57 | 1.65 |
| OLEIC (18:1n9) | 37.57 | 48.01 |
| LINOLEIC (18:2n6) | 16.04 | 15.90 |
| GAMMA-LINOLENIC (18:3n6) | 2.36 | 0.00 |
| ALPHA-LINOLENIC (18:3n3) | 3.00 | 4.03 |
| STEARIDONIC (18:4n3) | 0.45 | 0.00 |
| ARACHIDIC (20:0) | 0.29 | 0.38 |
| EICOSENOIC (20:1n9) | 1.14 | 0.85 |
| EICOSADIENOIC (20:2n6) | 0.02 | 0.00 |
| ARACHIDONIC (20:4n6) | 0.08 | 0.00 |
| EICOSAPENTAENOIC (20:5n3) | 2.85 | 0.00 |
| ERUCIC (22:1n9) | 0.64 | 0.39 |
| DOCOSAPENTAENOIC (22:5n3) | 0.17 | 0.00 |
| DOCOSAHEXAENOIC (22:6n3) | 1.12 | 0.00 |
| NERVONIC (24:1n9) | 0.26 | 0.14 |
| OTHERS | 1.55 | 0.39 |
| TOTAL | 100.00 | 100.00 |

TABLE 10

CHARACTERISTICS OF OIL BLENDS OF PREFERRED PRODUCTS

| INGREDIENT | DIET-14 | DIETS 15, 16 & 17 |
|---|---|---|
| % n-3 fatty acids | 7.59 | 4.03 |
| % n-6 fatty acids | 18.49 | 15.90 |
| % n-9 fatty acids | 39.60 | 49.39 |
| % saturated fatty acids | 31.64 | 30.18 |
| % monounsaturated fatty acids | 40.73 | 49.50 |
| % polyunsaturated fatty acids | 26.08 | 19.94 |
| % n-6/n-3 ratio | 2.44 | 3.94 |
| 8:2n6/18:3n3 ratio | 5.35 | 3.94 |
| 18:3n3, % total energy | 2.25 | 3.02 |
| 18:2n6, % total energy | 12.03 | 11.93 |
| 18:1n9, % total energy | 28.18 | 36.00 |
| PUFAs, % total calories | 19.56 | 14.95 |
| saturated fatty acids, % total calories | 23.73 | 22.63 |

It is believed that a nutritional product in accordance with the present invention should contain an oil blend in which the ratio of n-6 to n-3 fatty acids is in the range of 1 to 6, preferably 1.5 to 5, and most preferably 2 to 4.

TABLE 11

NUTRITIONAL PROFILES OF PREFERRED EMBODIMENTS (AS % OF TOTAL CALORIES)

| NUTRIENT | DIET 14 | DIET 15 | DIET 16 | DIET 17 |
|---|---|---|---|---|
| PROTEIN | 24.7 | 24.5 | 17.2 | 25.1 |
| FAT | | | | |
| MCT | 16.4 | 16.5 | 18.1 | 9.8 |
| LCT | 57.1 | 57.6 | 63.2 | 34.1 |
| TOTAL FAT | 73.4 | 74.1 | 81.3 | 43.9 |
| 1,3 BUTANEDIOL | NAP | NAP | NAP | 31.0 |
| CARBOHYDRATE | 1.9 | 1.4 | 1.6 | 0.0 |
| TOTAL | 100.0 | 100.0 10-0.0 | 100.0 | |

An enteral nutritional product in accordance with the present invention has 15% to 30% of the total calories provided by protein, 70% to 85% of the total calories provided by fat, and less than 5%, preferably less than 2%, of the total calories provided by carbohydrate.

TABLE 12

NUTRITIONAL ANALYSIS OF PREFERRED EMBODIMENTS

| NUTRIENT | UNITS | DIET 14 | DIET 15 | DIET 16 | DIET 17 |
|---|---|---|---|---|---|
| Total Solids | g/L | 240.4 | 237.3 | 224.9 | 243.2 |
| Protein | g/L | 94.1 | 92.8 | 66.1 | 93.6 |
| Fat | g/L | 126.9 | 127.2 | 141.7 | 74.3 |
| 1,3-butanediol | g/L | NAP | NAP | NAP | 77.2 |
| Ash | g/L | 12.1 | 11.8 | 11.1 | 11.7 |
| Carbohydrate (by difference) | g/L | 7.31 | 5.44 | 6.02 | 0[−13.7] |
| Density | g/L | 1030 | 1028 | 1020 | 1033 |
| Calcium | mg/L | 1205 | 1110 | 1071 | 1064 |
| Sodium | mg/L | 1369 | 1346 | 1346 | 1364 |
| Potassium | mg/L | 2337 | 2282 | 2040 | 2325 |
| Magnesium | mg/L | 470 | 458 | 422 | 437 |
| Phosphorus | mg/L | 1359 | 1326 | 1244 | 1261 |
| Chloride | mg/L | 1730 | 1706 | 1683 | 1798 |
| Zinc | mg/L | 27.3 | 29.5 | 26.9 | 29.6 |
| Vitamin C | mg/L | 436 | 448 | 447 | 465 |
| Pyridoxine | mg/L | 3.98 | 4.75 | 6.11 | 5.39 |
| Vitamin A | IU/L | 7094 | 6785 | 6170 | 7358 |
| Vitamin E | IU/L | 330.4 | 289 | 265.9 | 296.8 |

An enteral nutritional product according to the present invention contains all of the nutritional elements necessary to provide complete nutrition if fed to a head trauma patient as a sole source of nutrition.

TABLE 13

PHYSICAL STABILITY RESULTS OF PREFERRED EMBODIMENTS

| ASSAY UNITS | DIET 14 | DIET 15 | DIET 16 | DIET 17 |
|---|---|---|---|---|
| GRAIN[a] | 1 | 1 | 1 | 1 |
| pH | 6.69 | 6.71 | 6.78 | 6.73 |
| VISCOSITY cps | 108 | 122 | 24.4 | 65.6 |

Grain is a qualitative descriptor of protein stability with a value of 1 being best and a value of 6 being worst.

Clinical investigators using the nutritional products identified as Diets 14, 15, 16 and 17 will begin in the very near future and data supporting the beneficial properties of the instant invention will be provided. It is expected that this data will confirm that infract volume will be minimized.

A liquid nutritional product for enteral feeding according to a most preferred embodiment would be of maximum caloric density to minimize water intake and of low viscosity to facilitate enteral feeding. As shown above in Table 13, the viscosities of Diets 14 and 15 are both quite high, and would not be acceptable for tube feeding of a head trauma victim. A lower viscosity product has been manufactured with a caloric density of about 2000 kcal/L using a blend of non-hydrolyzed (intact) protein and protein hydrolysates. These products contained a partially hydrolyzed soy protein which was obtained from Protein Technology International, St. Louis, Mo. U.S.A. and was hydrolyzed to DH11 by a process which is proprietary to the protein supplier. The intact protein aids the production and stabilization of the oil-in-water emulsion whereas the protein hydrolysate provides the necessary amino acids without significant contribution to the viscosity. The experimental diets are described in Table 14.

TABLE 14

MOST PREFERRED EMBODIMENTS

| Exemplary Product | A | B |
|---|---|---|
| Total Protein, g/Kg | 129 | 121 |
| Protein from Hydrolysate, g/Kg | 90 | 90 |
| Intact Protein, g/Kg | 39 | 48 |
| Fat, g/Kg | 172 | 162 |
| Caloric Density, kcal/L | 2123 | 2001 |
| pH | 6.90 | 7.02 |
| Grain | 1 | 1 |
| Viscosity, cps | 36.6 | 72.9 |

Additional emulsification aids can also be incorporated such as but not limited to: mono-diglycerides, diacetyl tartaric acid esters of monoglycerides, sodium stearyl lactylate, soy lecithin, zanthan gum, gum arabic, and carrageenans.

An enteral nutritional product in accordance with the most preferred embodiments of the present invention contains by weight about 5% to 70% (preferably 30%) intact protein, and about 30% to 95% (preferably about 70%) partially hydrolyzed protein. While certain representative embodiments and details have been shown for the purpose of illustrating the invention, it will be apparent to those skilled in the art that various changes and modifications may be made therein without departing from the spirit or scope of the invention.

We claim:

1. An enteral nutritional product comprising a lipid blend having a ratio of n-6 to n-3 fatty acids in the range of 1 to 6, about 15% to 30% of the calories provided by the nutritional product being supplied by protein, about 70% to 85% of the calories provided by the nutritional product being supplied by fat, and less than 5% of the calories provided by the nutritional product being supplied by carbohydrate.

2. An enteral nutritional product according to claim 1 further comprising at least one nutrient having antioxidant properties selected from the group consisting of beta-carotene, vitamin E, vitamin C, taurine, molybdenum and selenium.

3. An enteral nutritional product according to claim 1 having a caloric density of 1 to 3 kcal/ml.

4. An enteral product according to claim 2 having a caloric density of 1 to 3 kcal/ml.

5. An enteral product according to claim 1 having a caloric density of 1.5 to 2 kcal/ml.

6. An enteral nutritional product according to claim 2 having a caloric density of 1.5 to 2 kcal/ml.

7. An enteral nutritional product according to claim 1 wherein the protein comprises about 5% to 70% intact protein and about 30% to 95% partially hydrolyzed protein.

8. An enteral nutritional product according to claim 2 wherein the protein comprises about 5% to 70% intact protein and about 30% to 95% partially hydrolyzed protein.

9. An enteral nutritional according to claim 3 wherein the protein comprises about 5% to 70% intact protein and about 30% to 95% partially hydrolyzed protein.

10. An enteral nutritional product according to claim 4 wherein the protein comprises about 5% to 70% intact protein and about 30% to 95% partially hydrolyzed protein.

11. An enteral nutritional product according to claim 5 wherein the protein comprises about 5% to 70% intact protein and about 30% to 95% partially hydrolyzed protein.

12. An enteral nutritional product according to claim 6 wherein the protein comprises about 5% to 70% intact protein and about 30% to 95% partially hydrolyzed protein.

13. An enteral nutritional product according to any one of claims 1 through 12 wherein the lipid blend comprises a combination of two or more ingredients selected from the group consisting of canola oil, soybean oil, medium chain triglycerides, high oleic safflower oil, high oleic sunflower oil, borage oil, fish oil, corn oil, fungal oils, algal oils, monoglycerides, phospholipids, diglycerides, ethyl or methyl esters of fatty acids and free fatty acids.

14. An enteral nutritional product according to anyone of claims 1 through 12 further comprising a source of dietary fiber.

15. An enteral nutritional product according to any one of claims 1 through 12 wherein the nutritional product has a viscosity suitable for tube feeding.

16. An enteral nutritional product according to any one of claims 1 through 12 wherein the lipid blend has a ratio of n-6 to n-3 fatty acids in the range of 1.5 to 5.

17. An enteral nutritional product according to any one of claims 1 through 12 wherein the lipid blend has a ratio of n-6 to n-3 fatty acids in the range of 2 to 4.

18. An enteral nutritional product according to any one of claims 1 through 12 wherein less than 2% of the calories provided by the nutritional product are supplied by carbohydrate.

19. An enteral nutritional product according to claim 17 wherein less than 2% of the calories provided by the nutritional product are supplied by carbohydrate.

* * * * *

UNITED STATES PATENT AND TRADEMARK OFFICE
CERTIFICATE OF CORRECTION

PATENT NO. : 5,308,832
DATED : May 3, 1994
INVENTOR(S) : K. Garleb, S. DeMichele, L. Rausch, M. Fuller, S. Behr It is certified that error appears in the above-identified patent and that said Letters Patent is hereby corrected as shown below:

Column 3, line 2 "tactic" should be --lactic--.

Column 3, line 56, "Maizet al.," should be --Maiz et al.--.

Column 17, line 15, "infract" should be --infarct--.

column 18, line 40, delete "to claim".

Signed and Sealed this

Twentieth Day of September, 1994

Attest:

BRUCE LEHMAN

*Attesting Officer*  *Commissioner of Patents and Trademarks*